United States Patent [19]

Brown, Jr.

[11] 4,378,431

[45] Mar. 29, 1983

[54] PRODUCTION OF A CELLULOSE-SYNTHETIC POLYMER COMPOSITE FIBER

[75] Inventor: Richard M. Brown, Jr., Chapel Hill, N.C.

[73] Assignee: The University of N.C. at Chapel Hill, Chapel Hill, N.C.

[21] Appl. No.: 183,310

[22] Filed: Sep. 2, 1980

[51] Int. Cl.$^3$ .................... C12P 19/04; C12R 1/02
[52] U.S. Cl. .................... 435/101; 435/823; 428/264; 428/265; 428/289; 428/481; 428/479.3; 428/478.4
[58] Field of Search .............. 435/101, 277, 823; 428/264, 265, 289, 478.4, 479.3, 481, 507

[56] References Cited

U.S. PATENT DOCUMENTS

| | | | |
|---|---|---|---|
| 3,450,555 | 6/1969 | Bridgeford | 428/264 |
| 3,916,447 | 11/1975 | Thompson | 428/507 X |
| 4,320,198 | 3/1982 | Mynatt | 435/101 |

OTHER PUBLICATIONS

Ohfuka et al., Chemical Abstracts, 77:153739n, p. 85, (1972).
Correns et al., Chemical Abstracts, 78:45330j, p. 96, (1973).
Fujishige et al., Chemical Abstracts, 86:91715b, p. 112, (1977).

*Primary Examiner*—Esther M. Kepplinger
*Attorney, Agent, or Firm*—Cushman, Darby & Cushman

[57] ABSTRACT

Hydrophilic characteristics are imparted to hydrophobic synthetic substrates, such as polyester fibers, by incubating a culture medium with Acetobacter bacterium in the presence of the substrate.

11 Claims, No Drawings

PRODUCTION OF A CELLULOSE-SYNTHETIC POLYMER COMPOSITE FIBER

BACKGROUND OF THE INVENTION

The present invention relates to a method of imparting hydrophilic characteristics to hydrophobic synthetic substrates, such as polyester fibers.

Many synthetic fibers, while having exceedingly useful properties such as durability, permanent press, etc. still lack some of the physical properties desired in a cotton fabric. One of the most notable properties is the hydrophilicity of a cotton fiber. The present invention takes advantage of the cellulose produced by Acetobacter in that it is possible to produce cellulose on the surface of the polyester fiber, thereby giving to the fiber many of the physical properties similar to the cotton fiber. The advantages of the cellulose-synthetic polymer composite are obvious:

(a) greater hydrophilicity and subsequent greater comfort in wearability;
(b) greater absorbancy which may be a useful property for disposal bandages, dressings, and the like;
(c) a natural biosynthetic reaction has been coupled onto the surface of a synthetic polymer as a substrate; and
(d) the altered surface properties of the cellulose-synthetic polymer composite might be advantageous for dyes or several other agents to the surface.

The gram negative bacterium, *Acetobacter xylinum*, is known to be capable of synthesizing a ribbon comprised of cellulosic microfibrils. Ribbons are generated at the gas-liquid interface of a standing culture. Intertwining ribbons of cellulose produce a thick membrane known as the pellicle. This pellicle is very hydrophilic and has great wet tensile strength.

The bacterial genus Acetobacter is differentiated from other Pseudomonadaceae by its ability to oxidize significant quantities of acetic acid under neutral and acid conditions. The species *A. xylinum* is characterized by the production of a thick, leathery cellulosic membrane or pellicle under aerobic conditions and on the surface of liquids containing suitable nutrients. Cells of this bacterium are elipsoidal to rod shaped, 0.6–8, with typical gram-negative walls for structures. The envelope consists of an outer lipopolysaccharide membrane and a plasma membrane with a peptidoglycan layer sandwiched in between. No capsule is present. *A. xylinum*, as well as other species of Acetobacter, is particularly prone to mutation, as purified strains become mixtures of two or more "species" after laboratory maintenance by serial transfer.

It is thus a primary object of the present invention to provide a means for imparting hydrophilic characteristics to hydrophobic substances.

A further object of the present invention provides for the modification of hydrophilic substances to enhance the hydrophilic properties thereof.

DETAILED DESCRIPTION OF THE INVENTION

The present invention provides for a method for imparting hydrophilic characteristics to hydrophobic substances which comprises incubating a culture medium inoculated with an Acetobacter bacterium capable of synthesizing cellulose microfibrils, in the presence of a synthetic substrate whereby cellulose microfibrils are produced on and attached to the surface of said substrate.

Suitable substrates include such synthetics as polyester, nylon and various plastics. Preferably (from the standpoint of textile manufacturing), the substrate is in the form of a fiber, which if desired may be woven or nonwoven.

As an alternative embodiment, the present invention provides for a method of enhancing the hydrophilic characteristics of hydrophilic substances (e.g. cotton or paper) by incubating a culture medium inoculated with an Acetobacter bacterium capable of synthesizing cellulose microfibrils, in the presence of a natural substrate whereby cellulose microfibrils are produced on and attached to the surface of the substrate.

Suitable natural substrates include materials as cotton (e.g. to increase the hydrophilic nature) and paper (e.g. to increase the strength). As with the synthetic substrates, preferably the natural is in the form of a fiber and may be a woven or nonwoven composite.

Incubation of the bacterium according to the present invention is carried out in a conventional manner except for the presence of the synthetic substrate which results in attachment of cellulose microfibrils to the substrate.

*Acetobacter xylinum* is widely distributed in nature. Strains may be obtained from fermenting sweet plant juices or rotting sugary fruits and vegetables. Cultures have been maintained in the laboratory in various media, including fortified coconut milk, hydrolyzed molasses with ammonia, and sucrose sweet beer. The pellicle generated may be thick or thin depending on the strain, and is characterized by a multiplicity of microfibrils. The present invention is thus suitable for any Acetobacter bacterium capable of generating microbial cellulose, including for example *A. acetigenum*.

Acetobacter bacteria enjoy the unique property of being able to weave and interdigitate with fiber substrates, including woven and nonwoven. The combination of pellicle and substrate in accordance with the present invention not only results in imparting or enhancing hydrophilic characteristics of the substrate, but further provides all the properties of cellulose, such as hand, dyeability, and added strength.

If desired, the modified substrates may be subjected to a posttreatment after attachment of cellulose microfibrils. For example, the modified substrate may be subjected to aldehyde treatment or cyanogen bromide treatment to alter the fiber characteristics as desired (e.g. to add specific functional or reactive groups). Such cellulose fiber fixing treatments are well known and conventional in the textile industry.

Most current research cultures of *A. xylinum* are maintained on a nutrient medium developed by Hestrin and Schramm, and consists of the following (%, w/v):

| | |
|---|---|
| glucose | 2.0 |
| peptone | 0.5 |
| yeast extract | 0.5 |
| disodium phosphate | 0.27 |
| citric acid | 0.11 |

The pH is adjusted to 6.0 with dilute HCl or NaOH.

The usual carbon source for cellulose synthesis is glucose, and it has been determined that more than 78% of the carbon in the cellulosic polymer is derived from exogenously added glucose.

Other carbon sources can be utilized to form cellulose. It is known that fructose followed by manitol, glucose, and glycerol, give rise to the highest yield of pellicle formation. No cellulosic pellicle is formed when the *A. xylinum* strain is supplied with pentoses such as arabinose and xylose, glycols, polyglycols, or erythritol. The saccharides lactose, sucrose, and maltose support cellulosic pellicle formation but with lower yields than from fructose or glucose.

Strains of *A. xylinum* have been isolated which grow on ethanol and are able to transform citric acid intermediates into cellulose. While ethanol is not utilized normally as a carbon source, the addition of a small amount to cultures can greatly increase pellicle yield.

A nitrogen source is necessary for cell growth, and metabolism, which in turn is necessary for the good production of pellicle, with the ammonium form favoring thick pellicle formation. One of the major problems with inorganic nitrogen is that some strains cannot be sustained on continued transfers. Under such conditions, isoleucine, valine, and alanine are required for continued growth.

The optimum initial pH of culture medium for the production of thick pellicles ranges from 4.5–6.5 with growth reported to be inhibited above a pH of 7.0 or 7.5, or below 3.5. The variation of acidity levels of cultures can vary during growth, but the addition of neutralizing agents to the cultures to control this variation can increase pellicle yields by the order of 50%. The optimum temperature for thick pellicle formation is conveniently close to room temperature, 28°–31° C., but can also be carried out at temperatures as low as 5° C.

As long ago as 1886, A. J. Brown identified the pellicle of *Acetobacter xylinum* (which he named *Bacterium xylinum*) as being cellulosic. The zoogleal pellicle first appears at the gas-liquid interface of the culture. It is initially a very hydrated clear membrane. Later the membrane thickens and becomes translucent. After a few days incubation, the cellulosic pellicle is a tough, solid sheet often completely filling the growth vessel. Fresh pellicles have the consistency of a firm, hydrophilic gel. Treatment with hot NaOH dissolves the bacteria leaving behind the cellulose matrix as a colorless, soft translucent mass. When the pellicles are dried, they are converted into thin, tough, brittle sheets.

Electron microscopic examination of *A. xylinum* cellulose reveals uniform bundles of microfibrils in the form of ribbons. The ribbons have periodic twists. The ribbons are composed of approximately 46 microfibrils, each about 1.6×5.8 nm.

The cellulose formed by Acetobacter is a well known standard type, similar to the crystalline homopolymer group which has been represented classically by the alpha cellulose of cotton. The cellulose is also free of lignin, hemicellulose, pectin, or other encrusting substances. The cellulosic microfibrils accumulate exclusively in the extracellular phase where they form a hydrophilic membraneous pellicle. The gas-liquid interface as the site of pellicle formation permits the possibility of large scale cellulose membrane production. The endogenous rates of glucose polymerization are relatively low, and combining this feature with negligible oxygen uptake suggests a very efficient utilization of exogenous substrate into cellulose polymer. The cellulose can be readily freed from bacterial cells thereby separating product from substrate.

The following examples are offered in order to more fully illustrate the present invention, but are not to be construed as limiting the scope thereof.

EXAMPLE ONE

Polyester was placed into six Petri dishes saturated with liquid culture medium. Culture medium was inoculated with Acetobacter. Within two days of incubation, Acetobacter had generated microfibrils of cellulose not only on the surface of the polyester mat but also on the surface of the individual polyester fibers. Examination with light and electron microscopy revealed the presence of the bacterial cellulose on the surface of the polyester fiber.

EXAMPLE TWO

Into a shallow tray (18"×12"×4") is placed a liquid culture medium inoculated with Acetobacter. Thereafter, there is continuously fed a roll of polyester woven fabric in such a manner that the fabric is immersed into the culture medium for a period of time sufficient to allow attachment of the cellulose microfibrils (at least about 30 minutes). The fabric is taken up on a roll sequentially and permitted to dry while the next successive portion is immersed in the medium.

A variety of substrates can be utilized for cellulose synthesis increasing the potential flexibility of utilization of agricultural wastes. The simplicity of cellulose production at the gas-liquid interface suggests that large scale microbial cellulose production plants could be located near convenient and inexpensive substrates.

It can thus be seen that the present invention provides a unique application of the gel-like properties and completely extracellular microfibrils of microbial cellulose. The composite polymer produced according to the present invention and having altered physical properties provides a whole new approach to the manufacture of "cotton-like" goods.

As will be appreciated, various modifications and variations of the foregoing methods can be employed without departing from the spirit of the present invention or scope of the claims below. Furthermore, the present invention may comprise, consist or consist essentially of the hereinbefore stated materials and procedures.

I claim:

1. A method for imparting hydrophilic characteristics to hydrophobic substrates which comprises incubating a culture medium inoculated with an Acetobacter bacterium capable of synthesizing cellulose microfibrils, in the presence of a hydrophobic synthetic substrate whereby cellulose microfibrils are produced on and attached to the surface of said substrate.

2. The method of claim 1 wherein said hydrophobic synthetic substrate is in the form of a fiber.

3. The method of claim 1 wherein said substrate is a nonwoven composite of fibers.

4. The method of claim 1 wherein said substrate is woven.

5. The method of claims 1 or 2 wherein said synthetic substrate is a material selected from the group consisting of a polyester, nylon, and polyolefin.

6. A process for imparting hydrophilic characteristic to a polyester fiber which comprises bringing said fiber into contact with a culture medium inoculated with an Acetobacter bacterium capable of synthesizing cellulose microfibrils for a period of time sufficient to incubate said bacterium and thereby result in the physical attachment of said microfibrils to said fiber whereby a polyester fiber of enhanced hydrophilic characteristics is obtained.

7. A process for enhancing hydrophilic characteristics of a cotton fiber which comprises bringing said fiber into contact with a culture medium inoculated with an Acetobacter bacterium capable of synthesizing cellulose microfibrils for a period of time sufficient to incubate said bacterium and thereby result in the physical attachment of said microfibrils to said fiber whereby a cotton fiber of enhanced hydrophilic characteristics is obtained.

8. A method for enhancing hydrophilic characteristics of hydrophilic substrates which comprises incubating a culture medium inoculated with an Acetobacter bacterium capable of synthesizing cellulose microfibrils, in the presence of a solid hydrophilic substrate whereby cellulose microfibrils are produced on and attached to the surface of said substrate which is a blend of natural and synthetic fibers.

9. The method of claim 8 wherein said substrate is a nonwoven composite of fibers.

10. The method of claim 8 wherein said substrate is a composite of woven fibers.

11. The method of claim 8 wherein said natural substrate is a material selected from the group consisting of cotton and paper.

* * * * *